(12) United States Patent
Hino

(10) Patent No.: US 6,905,461 B2
(45) Date of Patent: Jun. 14, 2005

(54) BENDING CONTROL MECHANISM FOR ENDOSCOPE

(75) Inventor: Kazuhiko Hino, Saitama (JP)

(73) Assignee: Fuji Photo Optical Co., Ltd., Saitama (JP)

( * ) Notice: Subject to any disclaimer, the term of this patent is extended or adjusted under 35 U.S.C. 154(b) by 8 days.

(21) Appl. No.: 10/611,159

(22) Filed: Jul. 2, 2003

(65) Prior Publication Data

US 2004/0015054 A1 Jan. 22, 2004

(30) Foreign Application Priority Data

Jul. 5, 2002 (JP) .................................. 2002-196826

(51) Int. Cl.$^7$ ................................................ A61B 1/00
(52) U.S. Cl. ................................................... 600/146
(58) Field of Search ............................... 600/146–152, 600/434, 435, 585; 604/95.01, 95.04

(56) References Cited

U.S. PATENT DOCUMENTS

| | | | | |
|---|---|---|---|---|
| 4,483,326 A | * | 11/1984 | Yamaka et al. | 600/149 |
| 5,347,993 A | * | 9/1994 | Tanaka | 600/109 |
| 5,667,476 A | * | 9/1997 | Frassica et al. | 600/149 |
| 5,752,912 A | * | 5/1998 | Takahashi et al. | 600/149 |
| 5,996,670 A | * | 12/1999 | Igarashi | 160/133 |

* cited by examiner

Primary Examiner—Beverly M. Flanagan
(74) Attorney, Agent, or Firm—Rabin & Berdo, P.C.

(57) ABSTRACT

Disclosed is a bending control mechanism for an endoscope according to the invention, which is characterized in that the bending control mechanism includes a bending portion provided in an insertion portion of the endoscope; a bending wire extended out from the bending portion in order to control the bending portion; a pulley as made operable in link with a bending control lever through the shaft portion of the pulley, the bending control lever being provided in the control portion of the endoscope; a driving wire winding groove as spirally formed on the outer peripheral surface of the pulley as well as in the peripheral direction of the pulley; a driving wire wound around the driving wire winding groove of the pulley; a connection member connecting the driving wire with the bending wire; and a guide member provided in the control portion and including a connection member slidably mounted thereon, wherein in the state where the most driving wire is would round the pulley, a relative position between the pulley and the guide member is determined such that the extending direction of the driving wire is substantially in parallel with the guide surface of the guide member. With the constitution of the above bending control mechanism, there is no need for any excess force to be used for winding up the driving wire round the pulley by using the bending control lever, and it become possible to control the bending portion with smaller force. Thus, controllability of the endoscope is improved and also, durability of the driving wire is improved.

6 Claims, 11 Drawing Sheets

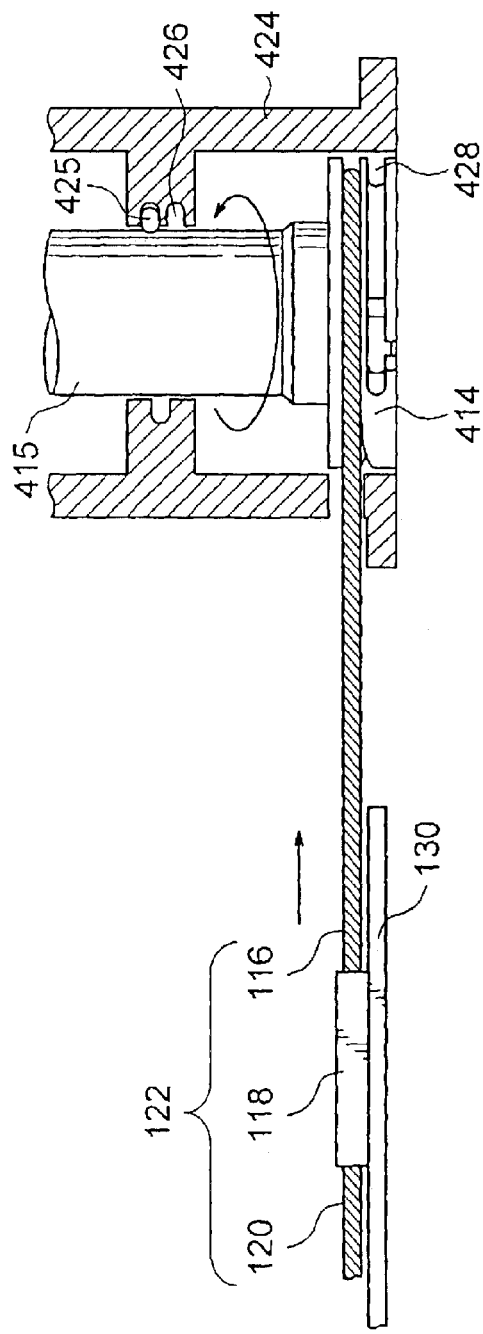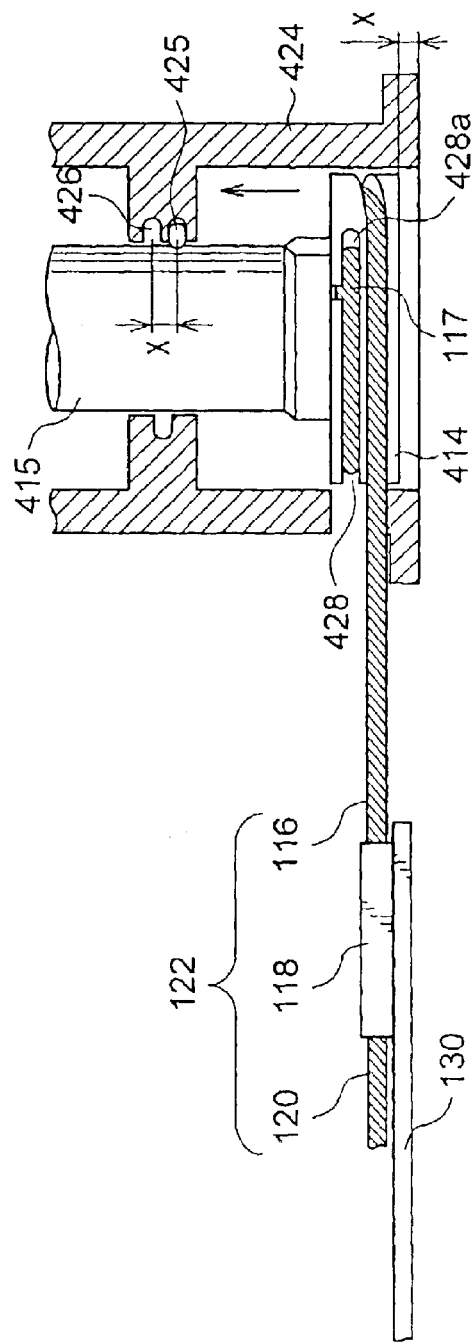

BENDING CONTROL MECHANISM FOR ENDOSCOPE

BACKGROUND OF THE INVENTION

The present invention relates to an endoscope for medical use and, more particularly, to a bending control mechanism which is built in the endoscope.

In general, the endoscope is composed of two main portions, of which one is a control portion and the other is a flexible insertion portion connected with the control portion and is inserted in the somatic cavity. The insertion portion includes a flexible soft portion connected with the control portion, a bent-free bending portion connected with the soft portion on the tip side of it, and a hard tip distal end portion which includes an objective window (lens) and others, is connected with the tip of the bending portion.

The endoscope is provided with a bending control mechanism for controlling the bending of the bending portion. This bending control mechanism includes a bending control lever, a pulley of which the rotational motion is controlled by the control lever, and a driving wire wound round (around) the pulley, all of the above lever, pulley, and driving wire being provided inside the control portion of the endoscope. The driving wire is connected with the bending wires through a connection member and functions as a control wire for controlling the bending portion.

The above pulley includes two juxtaposed independent grooves, each capable of winding up an independent driving wire (referred to as "driving wire winding groove" hereinafter). Here, if these two driving wires are wound round these driving wire winding grooves, one each in opposite winding directions, and then, the pulley is turned in one direction, one of two driving wires extending out from the pulley is taken up or wound up while the other is paid out or wound off from the pulley. Accordingly, two control wires connected with driving wires are controlled such that one advances and the other retreats, thus to carry out the bending control of the bending portion.

In the endoscope, however, in order to improve the observational performance, specifically to expand the area observable by the endoscope, it is desired to make a bending angle of the bending portion as large as possible. To meet the above desirable requirement, there is needed for the driving wire to have a large wire stroke.

Because of this, in order to make the wire stroke large, there has been proposed a prior art endoscope which increases the winding diameter of the pulley, round which the driving wire is wound. However, if the winding diameter of the pulley is made large, the turning torque of the pulley becomes large, which causes such inconvenience that the bending control lever requires greater force for controlling it.

On the other hand, in order to decrease the turning torque of the pulley, there is another prior art endoscope which makes the size of the pulley smaller by shortening the winding diameter of it. In the case of such a small pulley, however, as the winding diameter of the pulley is made shorter, the bending control lever has to be turned much more in order to obtain the same bending angle as obtained by the large pulley. Because of this, controllability of the bending portion is reduced.

Furthermore, in the pulley of which the winding diameter is made smaller, the more it is tried to make the stroke of the driving wire large, the more the excess driving wire has to be wound round the driving wire winding groove, for instance 2 turns or more. Because of this, the turning torque of the pulley gradually becomes larger corresponding to the number of turns of the driving wire, whereby bending control at a uniform turning torque becoming impossible. Still further, as the overlapped driving wires caused by double or more turned driving wires interfere with each, for instance rub against one another, the durability of the driving wire is reduced.

The invention has been made in view of such problems as described above. Accordingly, an object of the invention is to provide a bending control mechanism for the endoscope with high controllability, which can improve the durability of the driving wire wound round the pulley of the bending control mechanism and also enables the bending portion to be controlled with a smaller force.

SUMMARY OF THE INVENTION

In order to solve the problems as described above, according to the invention, there is provided a bending control mechanism for an endoscope, which is characterized in that the bending control mechanism includes a bending portion provided in an insertion portion of the endoscope; a bending wire extended out from the bending portion in order to control the bending portion; a pulley linked to a bending control lever through the shaft portion of the pulley, the bending control lever being provided in the control portion of the endoscope; a driving wire winding groove as spirally formed on the outer peripheral surface of the pulley as well as in the peripheral direction of the pulley; a driving wire wound round the driving wire winding groove of the pulley; a connection member connecting the driving wire with the bending wire; and a guide member provided in the control portion and including a connection member slidably mounted thereon, wherein in the state where the most driving wire is wound round the pulley (the driving wire is maximally wound around the pulley), a relative position between the pulley and the guide member is determined such that the extending direction of the driving wire is substantially in parallel with the guide surface of the guide member.

According to the invention like this, in the state where the tension applied to the driving wire wound round the pulley connected with the bending control lever is maximized while the bending portion control is carried out, as the extending direction of the driving wire is substantially in parallel with the guide surface of the guide member guiding the driving wire, there is no need for any excess force to be used for winding up the driving wire round the pulley by using the bending control lever, and the bending portion can be controlled with smaller force, whereby the controllability of the endoscope is improved.

Furthermore, in the state where the tension applied to the driving wire wound round the pulley is maximized while the bending portion control is carried out, as the driving wire is substantially in parallel with the guide surface of the guide member, it becomes possible to prevent the consumption or frictional wear of the driving wire caused by the rubbing motion between the driving wire and the wall face of the driving wire winding groove, which take place when winding the driving wire round the pulley. Consequently, there is improved the durability of the driving wire wound round the pulley of the bending control mechanism. With this, durability of the driving wire can be improved.

Furthermore, in the state where the most driving wire is wound round the pulley, the direction of spiral turn of the driving wire winding groove may be such a spiral turning direction that the extending direction of the driving wire becomes substantially parallel to the guide surface of the guide member. Like this, as the position in the axial direction of the driving wire extended out from the pulley can be changed by changing the direction of spiral turn of the driving wire winding groove, it becomes possible to make the extending direction of the driving wire be substantially in parallel with the guide surface of the guide member. Therefore, there is no need for the guide member to change its arrangement position and it is enough only to change the direction of spiral turn of the driving wire winding groove.

Still further, in the state where the most driving wire is wound round the pulley, the guide member may be arranged to be in such a position that the extending direction of the driving wire becomes substantially parallel to the guide surface of the guide member. With this, as the arrangement position of the guide member can be arranged to meet the position in the axial direction of the driving wire extended out from the pulley, it is possible to arrange the driving wire and the guide member such that the extending direction of the driving wire becomes substantially parallel to the guide face of the guide member. Therefore, there is no need for the driving wire winding groove to have its direction of spiral turn changed, and it is enough for the guide member only to change the arrangement position of it.

Still further, there may be provided a pulley displacement mechanism which displaces the pulley in the axial direction of it such that the extending direction of the driving wire becomes substantially parallel to the guide surface of the guide member, in correspondence with the height in the axial direction of the pulley of the driving wire wound round the pulley. As this pulley displacement mechanism makes it possible to produce such a state that the driving wire and the guide face of the guide member become always substantially parallel to each other, there is no need for any excess force to be used for winding up the driving wire round the pulley by using the bending control lever, and the bending portion can be controlled with smaller force. Also, it becomes possible to effectively prevent the consumption or frictional wear of the driving wire, which is caused by the rubbing motion between the driving wire and the wall face of the driving wire winding groove.

Still further, the pulley displacement mechanism may be provided with a cam groove formed on the shaft portion of the pulley, as well as a cam pin formed on the pulley support member for supporting the pulley so as to fit to the cam groove. Also, the pulley displacement mechanism may be provided with a cam formed on the pulley support member for supporting the pulley, as well as a cam pin formed on the shaft portion of the pulley so as to be fitted to the cam.

BRIEF DESCRIPTION OF THE DRAWINGS

The invention will now be described in detail by way of some preferred embodiments with reference to the accompanying drawings. In the following description and drawing, a constituent of the invention having substantially like function and constitution is designated by a like reference numeral or sign.

In the drawing:

FIG. 5A is an illustration showing an external appearance of the pulley and FIG. 5B is a sectional side view of the pulley.

FIGS. 11A and 11B are diagrams schematically showing the constitution and the operation of the bending control mechanism of the endoscope according to the fourth embodiment of the invention.

DETAILED DESCRIPTION OF THE PREFERRED EMBODIMENTS (First Embodiment)

Figure 1:
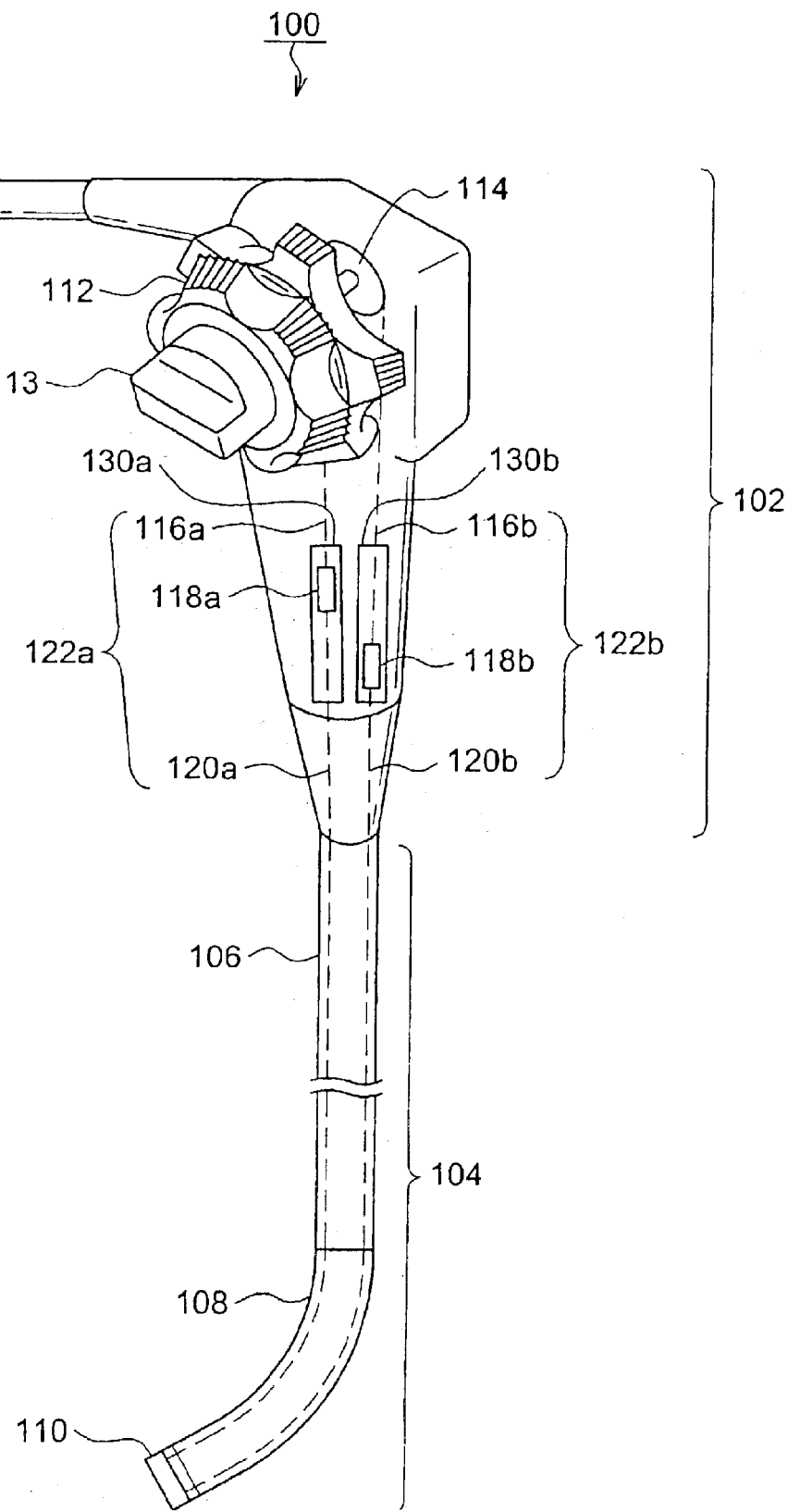
FIG. 1 is a perspective view showing a whole constitution of an endoscope according to the first embodiment of the invention.

First of all, there will be described an endoscope according to the first embodiment of the invention with reference to FIG. 1, which indicates the whole constitution of an endoscope according to the first embodiment of the invention. As shown in this figure, an endoscope 100 is composed of two principal portions, of which one is a control portion 102 and the other is a flexible insertion portion 104 connected with the control portion 102 and is inserted in the somatic cavity. The insertion portion 104 includes a flexible soft portion 106 connected with the control portion 102, a bend-free bending portion 108 connected with at the tip side of the soft portion 106, and a hard tip distal end portion 110 which is provided with an objective window (lens) and is connected with the tip of the bending portion 108.

In the control portion 102 of the endoscope 100, there is provided a bending control mechanism for controlling the bending of the above bending portion 108. This bending control mechanism is made up of a bending control lever 112, a pulley 114 rotated by the bending control lever 112, and a pair of driving wires 116a, 116b wound round the pulley 114, which are all provided in the control portion 102 of the endoscope 100. Driving wires 116a, 116b are connected with the bending wires 120a, 120b through connection members 118a, 118b slidably mounted on guide members 130a, 130b which are provided in the control portion 102. Consequently, driving wires 116a, 116b come to function as control wires 122a, 122b of the bending portion 108.

Figure 2:
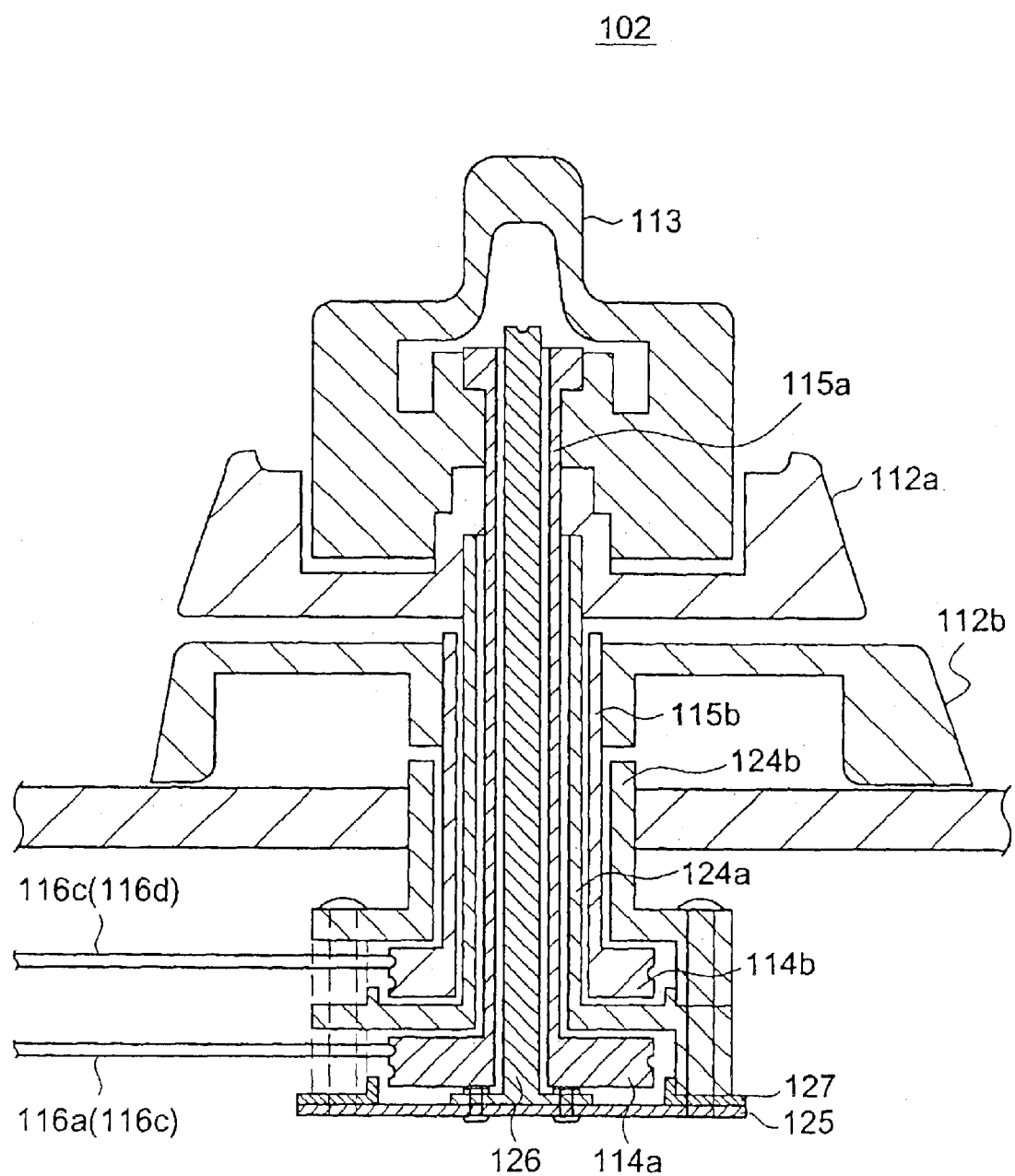
FIG. 2 is a sectional view showing the peripheral portion of a bending control lever in the endoscope control portion according to the first embodiment of the invention.
Figure 3:
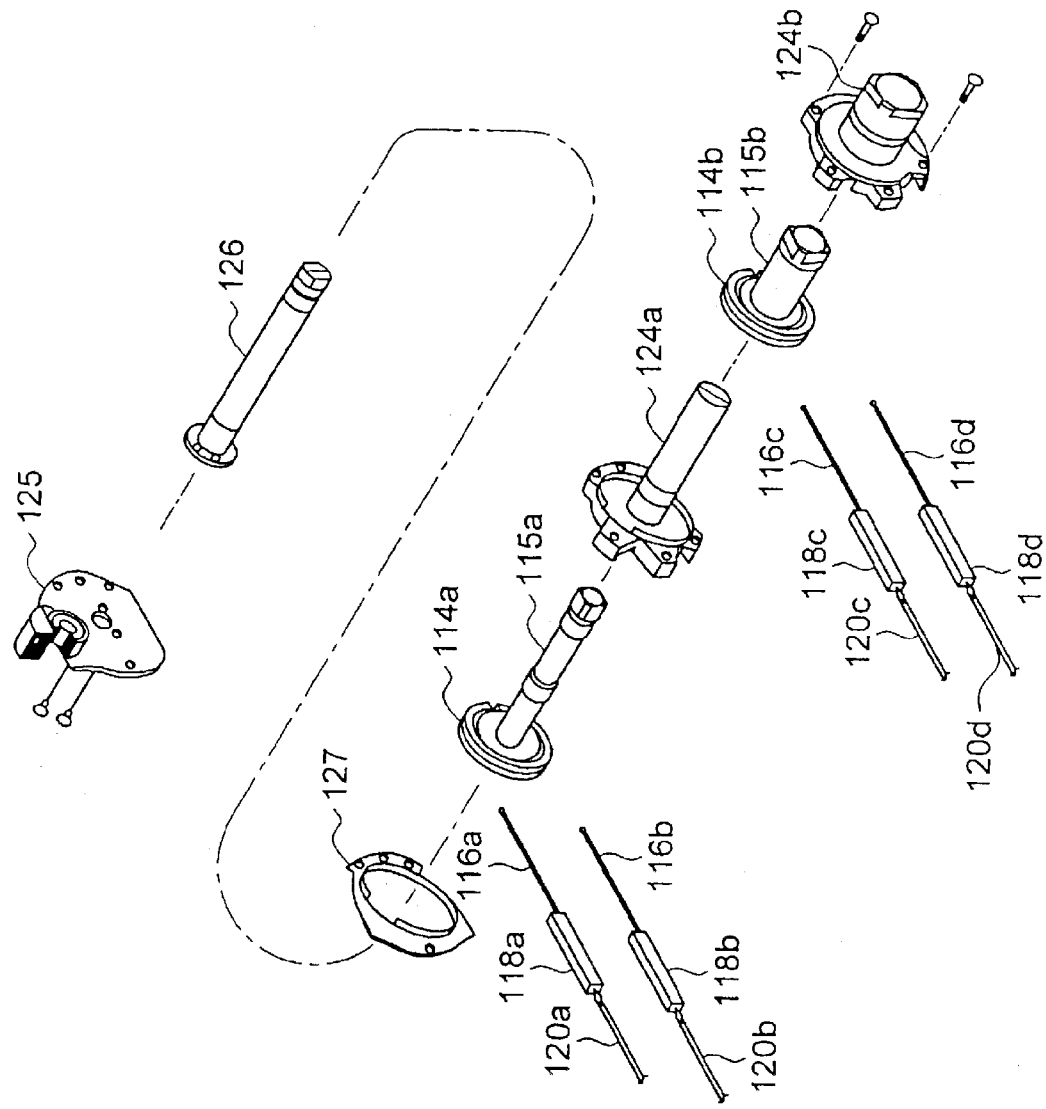
FIG. 3 is an exploded perspective view showing a pulley and a support member of the pulley in the endoscope control portion.
Figure 4:
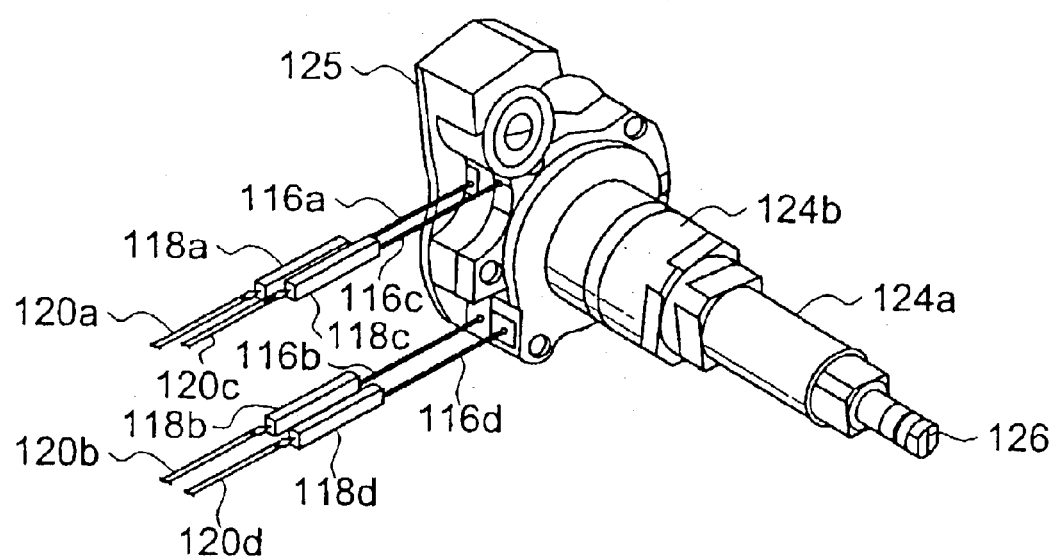
FIG. 4 is a perspective view showing a complete assembly of the pulley and the support member of the pulley as shown in FIG. 3.

FIG. 2 is a vertical sectional view schematically showing the state of connection between the bending control lever 112 and the pulley 114, which are provided in the control portion 102. FIG. 3 is an exploded perspective view showing the pulley 114 and a support member 124 of the pulley, while FIG. 4 is a perspective view showing a complete assembly of the pulley 114 and the support member 124 of the pulley as shown in FIG. 3. Here, an expression "bending control lever 112" represents a bending control lever 112a for right-left (RL) bending control (referred to as "RL bending control lever 112a" hereinafter) and a bending control lever 112b for up-down (UD) control (referred to as "UD bending control lever 112b" hereinafter). Also, an expression "pulley 114" represents a pulley 114a for RL control (referred to as "RL control pulley 14a" hereinafter) and a pulley 114b UD control (referred to as "UD pulley control 114b" hereinafter). Furthermore, an expression "pulley shaft portion 115" represents a pulley shaft portion 115a for RL control (referred to as "RL control pulley 115a" hereinafter) and a pulley shaft portion 115b for UD control (referred to as "UD control pulley shaft portion 115b" hereinafter) control. Still further, an expression "pulley support member 124" represents a pulley support member 124a for RL control (referred to as "RL pulley support member 124a" hereinafter) and a pulley support member 124b for UD control (referred to as "UD pulley support member 124b" hereinafter).

As shown in FIG. 3, a plate 125 for fixing a shaft (referred to as "shaft-fixing plate 125" hereinafter) arranged inside the above control portion 102 is immovably fitted with a fixed shaft 126, by means of screws or the like. Also, a ring-shaped pulley support member 127 is firmly fixed on the shaft-fixing plate125 by means of screws or the like, and the RL control pulley 114a is inserted along the fixed shaft 126 so as to be accepted inside the ring shaped pulley support member 127.

The RL control pulley support member 124a is inserted along the shaft portion 115a of the RL control pulley 114a while the UD control pulley 114b is inserted along the RL control pulley support member 124a. The UD pulley support member 124b is inserted along the shaft portion 115b of the UD control pulley 114b. The UD control pulley support member 124b is fixed on the shaft-fixing plate 125 by means of screws or the like through the RL control pulley support member 124a and the ring shaped pulley support member 127.

Driving wires 116a, 116b are wound round the RL control pulley 114a while driving wires 116c, 116d are wound round the UD control pulley 114b.

Furthermore, driving wires 116a, 116b, 116c and 116d are respectively connected with bending wirers 120a, 120b, 120c and 120d through connection members 118a, 118b, 118c and 118d, which are slidably arranged on a guide member 30 as shown in FIG. 8. The guide member 30 is arranged inside of the control portion 102.

As shown in FIG. 2, the shaft portion 115a of the RL control pulley 114a is connected with the RL bending control lever 112a while the shaft portion of the UD control pulley 114b is connected with the UD bending control lever 112b.

With the constitution as described above, if the bending control lever 112 is turned, the pulley 14 is turned through the pulley shaft portion 115. Therefore, the pulley 114 is turned by an angle corresponding to the angle of rotation of the bending control lever 112. For instance, if the RL bending control lever 112a is turned, the pulley shaft portion 115a is turned and then, the RL control pulley 114a is turned by an angle corresponding to the angle of rotation of RL bending control lever 112a. With this, the control wire 122 comes to go back and forth, whereby the bending portion 108 is made to move in the right or left direction.

Figure 5A:
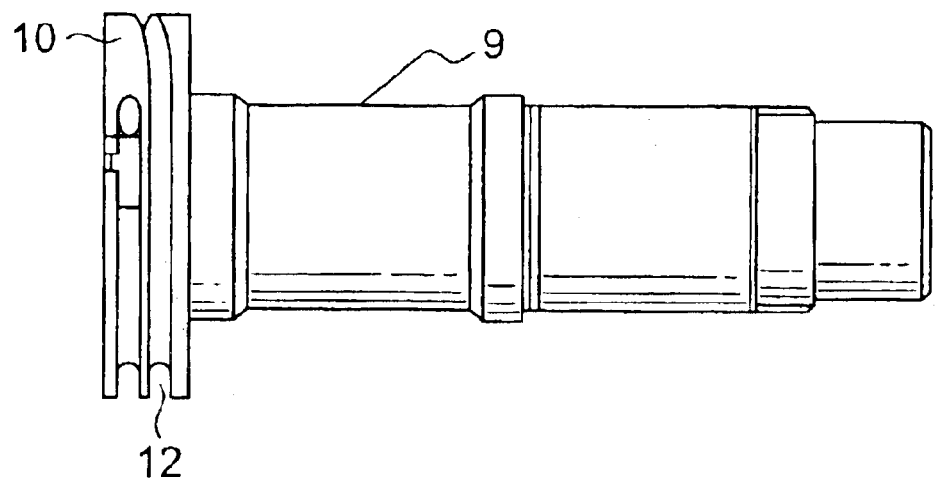
FIGS. 5A and 5B are diagrams showing the constitution of the pulley provided in a prior art endoscope.
Figure 5B:
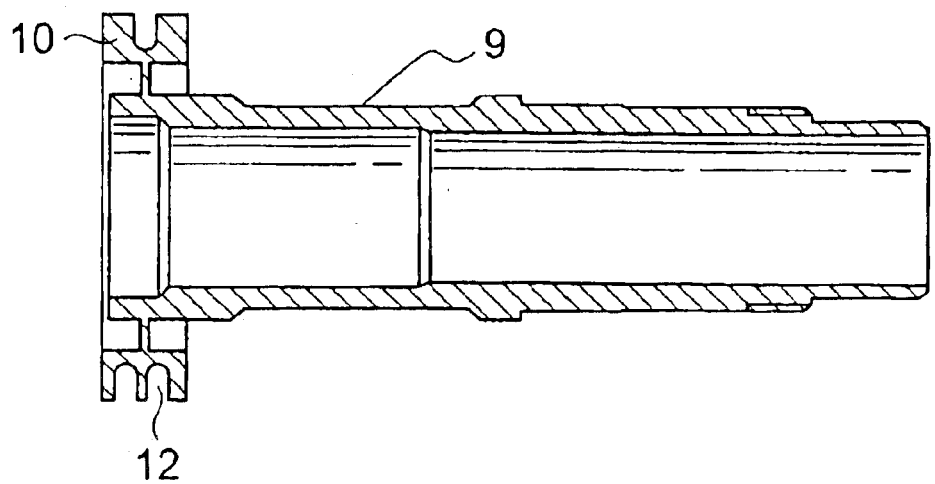
Figure 6A:
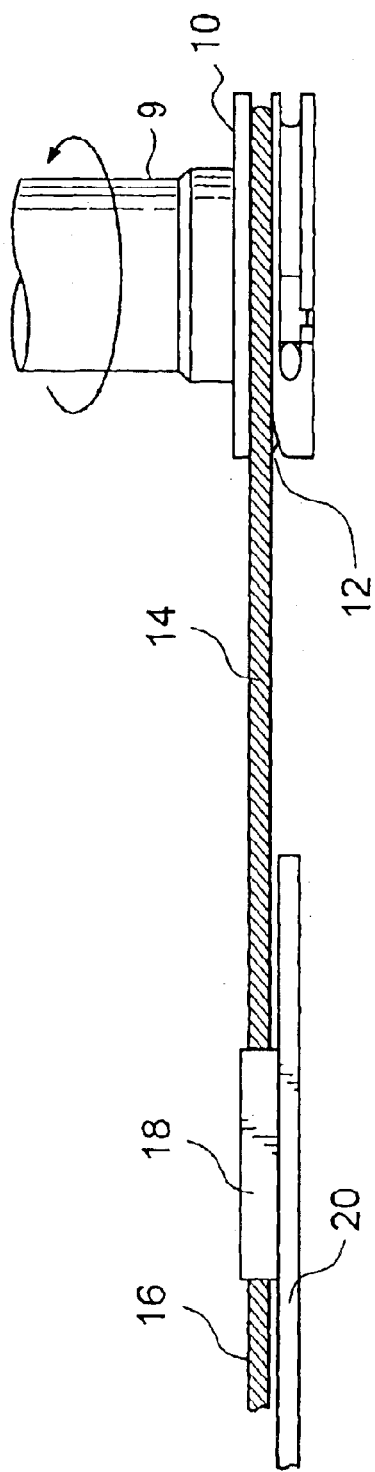
FIGS. 6A and 6B are diagrams schematically showing the constitution and the operation of the bending control mechanism of the prior art endoscope.
Figure 6B:
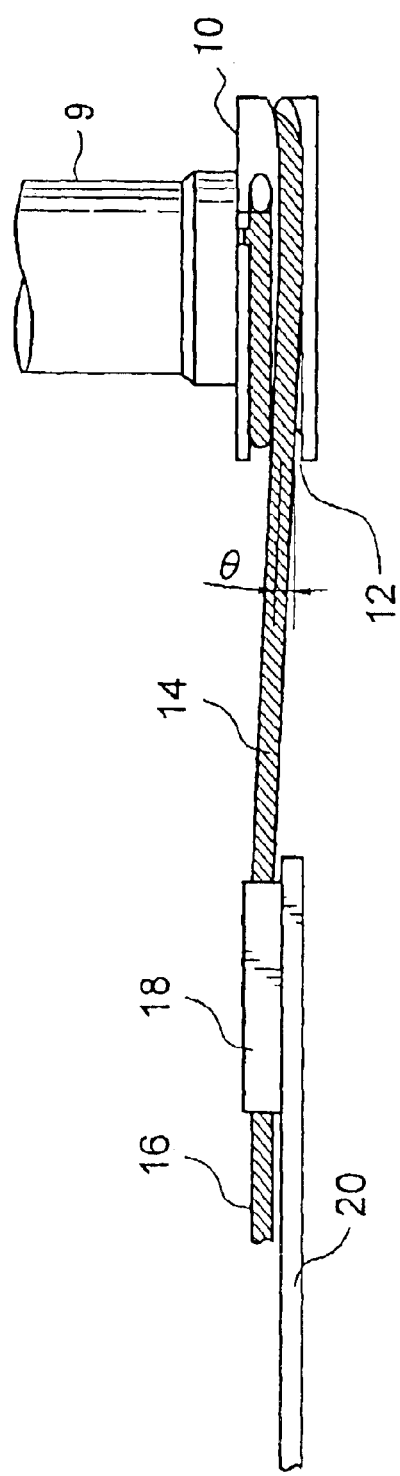

In the next, the pulley of the bending control mechanism according to the invention will be described in detail especially about the concrete constitution of the pulley as well as about the positional relation between the pulley and a guide member. First of all, let us start by comparing the pulley 114 of the bending control mechanism according to the invention with a prior art pulley with reference to the drawings. FIGS. 5A and 5B indicate the constitution of a prior art pulley 10 and FIGS. 6A and 6B show the positional relation between the pulley 10 and a prior art guide member 20. Here, the RL control pulley and the UD control pulley have substantially the same constitution and also, the RL control pulley shaft portion and the UD control pulley shaft portion have the substantially same constitution. Therefore, both of these pulleys and both of pulley shaft portions will be collectively referred to as the pulley 10 and the pulley shaft portion 9 in the following description.

As shown in FIGS. 5A and 5B, the pulley 10 is provided at one end portion of the pulley shaft portion 9. A groove 12, round (around) which a driving wire 14 is wound (referred to as "driving wire winding groove" hereinafter) is formed on the peripheral surface of the pulley 10. As shown in FIG. 5A, the driving wire winding groove 12 is formed in the shape of a spiral which continuously extends in the peripheral direction of the pulley 10. The driving wire winding groove 12 is formed such that a plurality of step grooves are formed in the axial direction of the shaft portion 9 from the end face of the pulley 10 toward the pulley shaft portion 9. The end portion of one driving wire is fixedly connected with the one end portion of the driving wire winding groove 12, while the end portion of the other driving wire is fixedly connected with the other end portion of the driving wire groove 12. FIGS. 6A and 6B indicates a state attained when winding the driving wire 14 round the driving wire winding groove 12 as described above. In these figures, however, only one driving wire is shown and the other one is omitted.

The driving wire 14 extending out from the pulley 10 is connected with a bending wire 16 through a connection member 18, which is slidably mounted on a guide member 20.

Consequently, if the pulley 10 like the above is rotated in one direction, one driving wire is taken up or wound up while the other one is paid out or wound off. Contrary to this, if the pulley 10 is rotated in the direction opposite to the above, the other driving wire is taken up (wound up) while one driving wire is paid out or wound off.

Accordingly, it can be avoided to wind the driving wire round the same driving wire winding groove 12 two or more times, that is, the so-called double winding can be avoided. This prevents the same driving wires from interfering with each other, which contributes to improvement of the durability of the driving wire.

Furthermore, as the driving wire winging groove 12 is formed in the shape of a spiral, it becomes possible to wind a longer driving wire 14. Thus, the winding diameter of the pulley 10 can be made larger, by which the rotational torque of the pulley 10 can be reduced. These effects of the spiral shaped driving wire winging groove 12 make it possible to provide a bending control mechanism with excellent controllability.

As described above, even the pulley 10 having a structure like the above can take sufficiently useful effects, but if the pulley 10 is able to overcome the following points, it will is able to assure more excellent controllability and more improved durability of the driving wire.

For example, in the case of the pulley 10, as the driving wire winding groove 12 is formed in the shape of a two-step spiral extending along the outer peripheral surface of the pulley 10 as well as in the axis direction of the shaft of the pulley 10, the extending direction of the driving wire 14 becomes different depending on two states. One is the state where the bending portion is not bent, the so-called neutral state as shown in FIG. 6A, and the other is the state where the bending portion is bent as shown in FIG. 6B. Because of this, there happens the case that the driving wire 14 as paid out from the driving wire winding groove 12 is not in substantially parallel with the guide surface of the guide member 20. For instance, as shown in FIG. 6A, even if the driving wire 14 paid out from the inner step groove (groove near the pulley shaft) of the driving wire winding groove 12 is set to be substantially in parallel with the guide surface of the guide member 20 in the neutral state, the substantial parallelism as set above between the guide surface of the guide member 20 and the driving wire 14 paid out from the outer step groove (groove near the pulley end surface) of the driving wire winding groove 12 is lost due to the displacement of the pulley 10 in the axial direction of its shaft as shown in FIG. 6B when the maximum tension (caused by the most wire winding) is applied to the driving wire. Accordingly, in case of FIG. 6B, as the angle θ of inclination is caused between the driving wire 14 and the guide member 20, the pulley 10 has to be rotated with an ordinary force plus $1/\cos^2 \theta$ of the wire tension.

(11)

Furthermore, the larger the angle of inclination between the driving wire 14 and the guide surface of the guide member 20 becomes, the more the driving wire 14 comes to strongly rub against the wall face of the driving wire winding groove 12 of the pulley 10, thus the durability of the driving wire 14 being damaged.

Therefore, in the invention, in the state where the most driving wire 116 is wound round the pulley 114, the extending direction of the driving wire 116 paid out from the pulley 114 is determined taking account of the position of the guide member 130 such that the extending direction of the driving wire 116 becomes substantially parallel to the guide surface of the guide member 130.

Figure 7A:
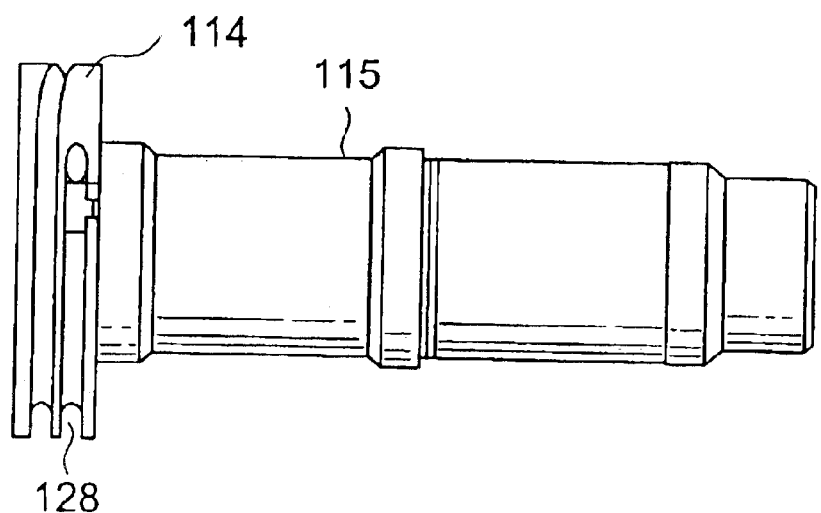
FIG. 7A is an illustration showing an external appearance of the pulley according to the first embodiment of the invention and FIG. 7B is a sectional side elevation of the pulley according to the first embodiment of the invention.
Figure 7B:
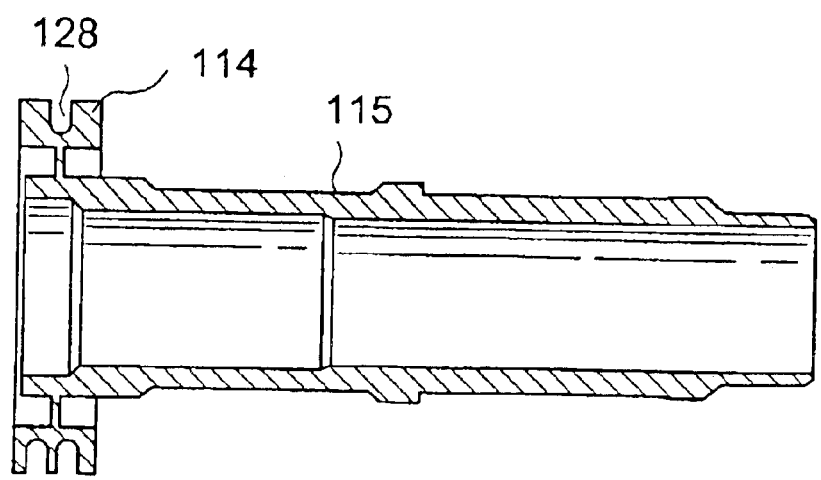

A pulley 114 of the bending control mechanism according to the invention as described above will now be described with reference to the accompanying drawings. FIGS. 7A and 7B are diagrams showing the constitution of the pulley 114 of the bending control mechanism according to the first embodiment of the invention in which FIG. 7A is an external view of the pulley 114 and FIG. 7B is a vertical sectional view of the pulley 114. Here, in this embodiment, as the RL control pulley and the UD control pulley have the substantially same constitution while the RL control pulley shaft portion and the UD control pulley shaft portion also have the substantially same constitution. Therefore, both of these pulleys and both of these pulley shaft portions will be collectively referred to as the pulley 114 and the pulley shaft portion 115 in the following description.

As shown in FIGS. 7A and 7B, the pulley 114 according to this embodiment is provided at the one end of the pulley shaft portion 115, which is formed in the substantially cylindrical shape. The other end (with which no pulley is fitted) of the pulley shaft portion 115 is fitted with the bending control lever 112.

As shown in FIG. 7A, the driving wire winding groove 128 for winding the driving wire 116 round itself is formed on the outer periphery of the pulley 114. The driving wire winding groove 128 is in the shape of a spiral continuously extending in the peripheral direction of the pulley 114. The driving wire winding groove 128 in this embodiment is also in the shape of a spiral continuously extending in the peripheral direction of the pulley 114, but the turning direction of this spiral is made opposite (anti-clockwise to the peripheral direction of the pulley 114) to that of the spiral of the driving wire winding groove 12 of the pulley 10 as shown in FIG. 5A. To put it concretely, the spiral groove of the driving wire winding groove 128 is formed such that a plurality of step grooves are formed in the direction from the pulley shaft portion 115 of the pulley 114 toward the end surface of the pulley 114.

One end portion 128a of the driving wire winding groove 128 is fixed to the end portion of one driving wire while the other end portion 128b of the driving wire winding groove 128 is fixed to the end portion of the other driving wire. The driving wire winding groove 128 and the driving wire winding groove 12 of the pulley 10 as shown in FIGS. 5A an 5B differ from each other in the point from which the winding of the driving wire 116 starts. In FIGS. 7A and 7B, the other driving wire is omitted.

The above driving wire 116 is wound round the pulley 114 which is provided so as to act in link with the bending control lever 112 provided in the control portion 102. If the bending control lever 112 is turned, the pulley shaft portion 115 is turned, thereby the pulley 114 being turned by an angle equal to the angle of rotation of the bending control lever 112. With this, the driving wire 116 is wound round the pulley 114 and the bending wire 120 connected with the driving wire 116 through the connection member 118 is pulled back in the direction toward the pulley 114, whereby the bending portion 108 is bent. The driving wire 116 is connected with the bending wire 120 through the connection member 118, and it functions as the control wire 122 of the bending portion 108.

As described above, the driving wire 116 is connected with the bending wire 120 through the connection member 118. The connection member 118 is mounted with the ability to slide on the guide member 130. The guide member 130 is provided between the pulley 114 and the insertion portion 104 of control portion 102. In this embodiment, the guide member 130 is arranged in advance such that, in the neutral state, the extending direction of the driving wire 116 is slanted to the guide face of the guide member 130. With this arrangement, when the most driving wire 116 is wound round the pulley 114, in other words, when the most force is applied to the driving wire 116 in the bending control operation, it becomes possible for the direction in which driving wire 116 is extended to be substantially in parallel with the guide face of the guide member 130.

Figure 8A:
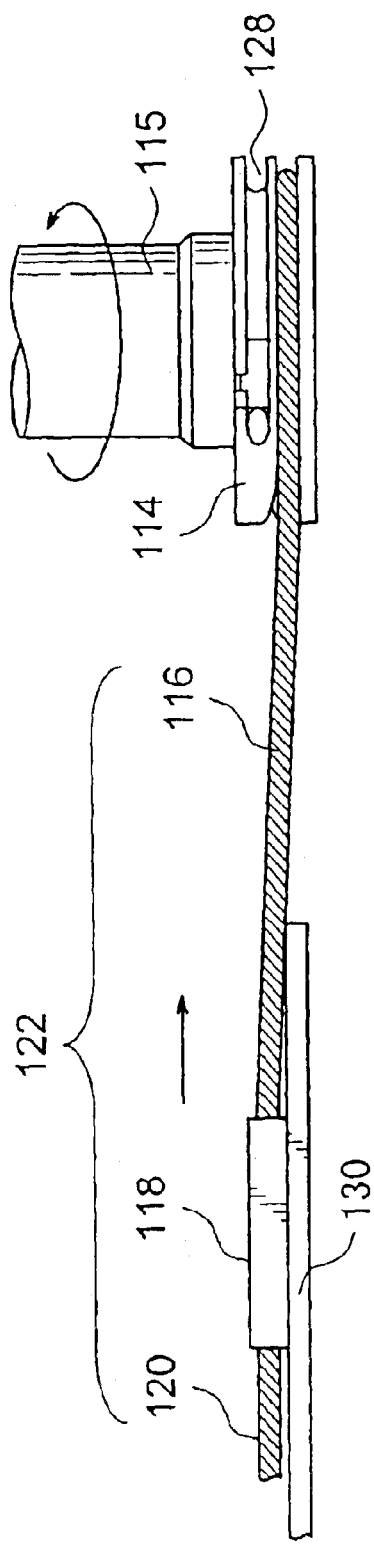
FIGS. 8A and 8B are diagrams schematically showing the constitution and the operation of the bending control mechanism of the endoscope according to the first embodiment of the invention.
Figure 8B:
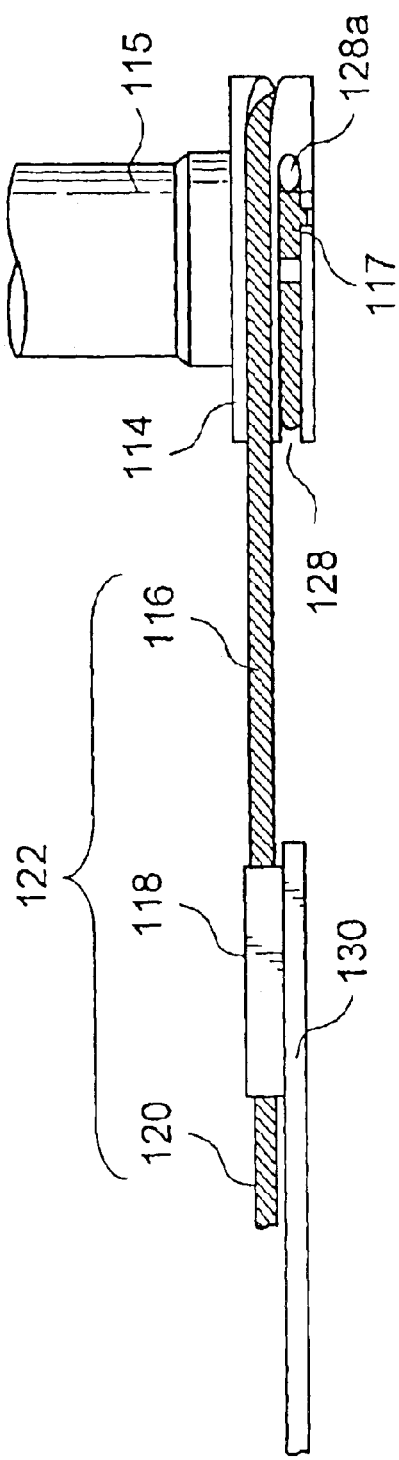

The following describes the operation of the bending control mechanism of the endoscope according to the first embodiment of the invention with reference to FIGS. 8A and 8B, in which FIG. 8A indicate the state of the bending control mechanism where the bending portion 108 is in the neutral state and FIG. 8B indicates the state of the bending control mechanism where the most driving wire 116 is wound round the pulley 114.

In the first embodiment, the driving wire winding groove 128 in the shape of an anti-clockwise spiral formed along the peripheral surface of the pulley 114, and the end portion 117 of the driving wire 116 is connected with the end portion 128a of the driving wire winding groove 128, the end portion 128a being located on the end surface side of the pulley 114. In the following description, an expression "pulley surface side" stands for the side where no pulley shaft portion is provided in the axial direction of the pulley while an expression "pulley shaft provision side" means the side where a pulley shaft portion is provided in the axial direction of the pulley.

Furthermore, in this embodiment, the spiral shaped driving wire winding groove 128 provided in he pulley 114 is made to turn anti-clockwise along the peripheral direction of the pulley 128 as shown in FIGS. 8A and 8B. The driving wire 116 is connected with the end portion 128a of the driving wire winding groove 128, the end portion 128a being located on the end surface side of the pulley 114. The guide member 130 is located such that in the neutral state, the direction in which driving wire 116 extends is slanted to the guide surface of the guide member 130.

Because of this arrangement, in the neutral state, the direction driving wire 116 extends can not be parallel with the guide surface of the guide member 130 as shown in FIG. 8A. On the other hand, when the most driving wire 116 is wound round the pulley 114 to the maximum as shown in FIG. 8B, the position of the pulley 114 in the axial direction of itself, at which the driving wire 116 is paid out through the driving wire winding groove 128, is substantially in the same height of the position of the connection member 118 on the guide member 130. Therefore, the extending direction of the driving wire 116 becomes substantially parallel to the guide surface of the guide member 130.

As described above, according to the first embodiment of the invention, in the state where the tension applied to the driving wire 116 is maximized, in other words, when the most driving wire is wound round the pulley 114, the relative position between the driving wire 116 and the guide member 130 is determined such that they becomes substantially parallel to each other. At this point, it becomes possible for the bending control lever 112 to rotate the pulley 114 for winding up the control wire 122 round it without using any extra force but with the smaller force, comparing with the pulley 10 of the bending control mechanism as shown in FIG. 5. Consequently, as the bending portion 108 can be controlled with smaller force, controllability of the endoscope is improved.

Furthermore, in the state where the tension applied to the driving wire 116 is maximized, in other words, when the most driving wire is wound round the pulley 114, as the driving wire 116 and the guide member 130 are held substantially in parallel with each other, it becomes possible to prevent the consumption or frictional wear of the driving wire which is caused by the rubbing motion between the driving wire 116 and the wall face of the driving wire winding groove 128, which takes place when winding the driving wire 116 when round the pulley 114. Thus, there can be improved the durability of the driving wire 116 wound round the pulley of the bending control mechanism.

(Second Embodiment)

Figure 9A:
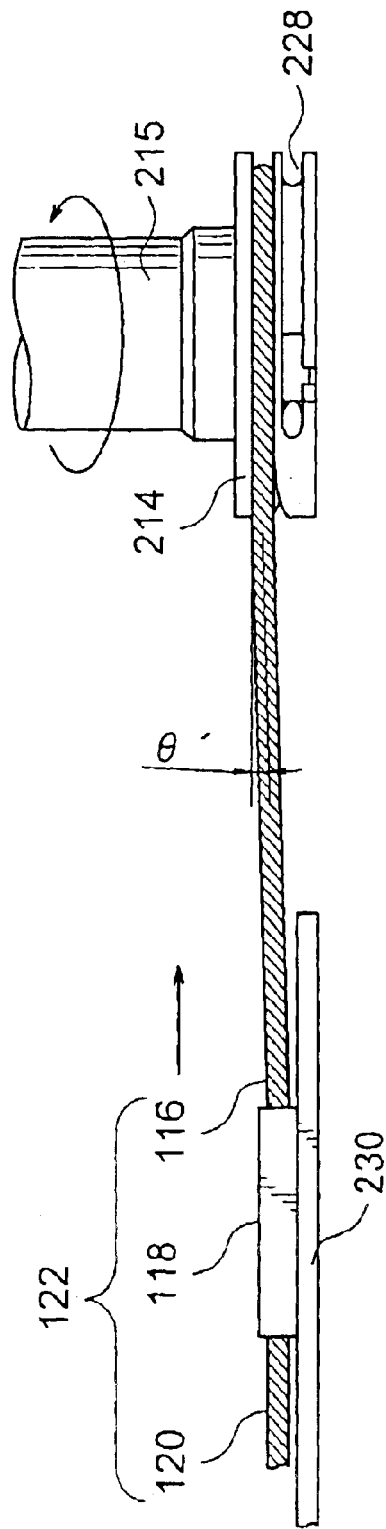
FIGS. 9A and 9B are diagrams schematically showing the constitution and the operation of the bending control mechanism of the endoscope according to the second embodiment of the invention.
Figure 9B:
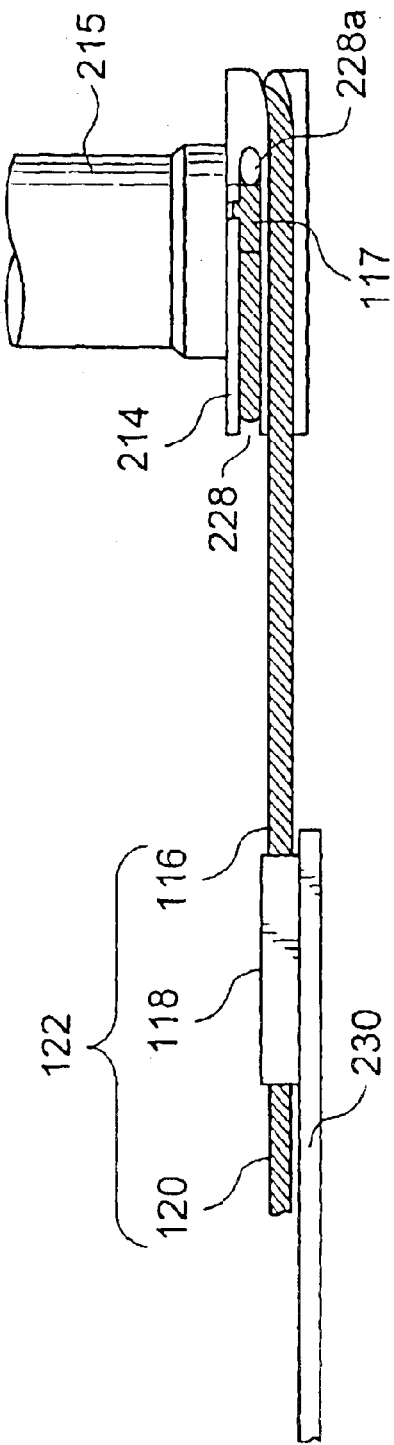

The following describes the bending control mechanism of the endoscope according to the second embodiment of the invention with reference to the accompanying drawings. FIGS. 9A and 9B are diagrams schematically showing the constitution and the operation of the bending control mechanism for the endoscope according to the second embodiment of the invention, in which FIG. 9A indicates the bending control mechanism staying in the neutral state (non-bending control) while FIG. 9B indicates the bending control mechanism staying in the state where the most driving wire 116 is wound round the pulley 214. The endoscope to which the bending control mechanism of this embodiment is applied is the same as the one described in the first embodiment. Thus a detailed explanation thereof has been omitted. This omission will be applied to the other embodiments as will be described later.

As shown in FIG. 9B, in the state where the most driving wire 116 is wound round the pulley 214, the bending control mechanism of the second embodiment differs from that of the first embodiment in the constitution of the pulley 214 as well as in the arrangement position of the guide member 230.

To put it more concretely, the pulley 214 of the second embodiment is provided with a driving wire winding groove 228 similarly to pulley 10 which possesses a driving wire winding groove 12 as shown in FIG. 5. That is, both of driving wire winding grooves 228 and 12 are similarly formed along the peripheral direction of respective pulley and in the shape of a clockwise spiral. Also, as shown in FIG. 9B, the end portion 117 of the driving wire 116 is connected with the end portion 228a of the driving wire winding groove 228 on the shaft-provision side of the pulley 214 and extends therefrom.

Furthermore, as shown in FIG. 9A, in the neutral state before the driving wire is wound up by the pulley 214, the connection member 118, which is mounted with the ability to slide on the guide member 230 provided inside the control portion, stays in the position that is deviated in the axial direction of the pulley 214 from the position out of which the driving wire 116 extends. At this time, the driving wire 116 makes an angle θ' with regard to the direction vertical to the axial direction of the pulley 214.

In this state, when the most driving wire 116 is wound, the position of the guide member 230 is determined such that the extending direction of the driving wire 116 and the guide face of the guide member 230 are substantially in parallel with each other. Like this, relative position between the pulley 214 and the guide member 230 is determined such that the extending direction of the driving wire 116 becomes parallel to the guide face of the guide member 230.

In the neutral state, because the guide member 230 is arranged as shown in FIG. 9A, the driving wire 116 can not be in parallel with the guide face of the guide member 230 in the neutral state but slopes up directing to the extending point of the driving wire 116 from the pulley 214 as shown in FIG. 9A. In contrast with this, in the state where the most driving wire 116 is wound round pulley 214 as shown in FIG. 9B, as the driving wire 116 is wound round the spiral-shaped driving wire winding groove 228 provided on the shaft-provision side of the pulley 214, the extending point of the driving wire from the driving wire winding groove 228 comes down until the same height level as that of the connecting member 118 mounted on the guide member 230 provided inside the control portion.

Because of this, when the most driving wire 116 is wound round the pulley 214, the extending direction of the driving wire 116 and the guide face of the guide member 230 become parallel with each other and at this time, the positional relation between the driving wire 116 and the guide member 230 is relatively determined. When the tension applied to the driving wire 116 is maximized, in other words, when the most driving wire 116 is wound round the pulley 214, the driving wire 116 becomes substantially parallel to the guide member 230. Accordingly, compared to the pulley 10 of the bending control mechanism as shown in FIG. 5, there is no need for any excess force to be used for winding up the driving wire 116 round the pulley 214, and it becomes possible to turn the bending control lever 112 with smaller force.

Besides, when the tension applied to the driving wire 116 is maximized, that is, when the most driving wire 116 is wound round the pulley 214, as the driving wire 116 and the guide member become substantially parallel to each other, it becomes possible to prevent the consumption or frictional wear of the driving wire caused by the rubbing motion between the driving wire 116 and the wall face of the driving wire winding groove 228, which takes place when winding the driving wire 116 round the pulley 214.

Furthermore, as there is no chance that the driving wire 116 is in contact with the guide member 230 even in the neutral state, it becomes possible to prevent the consumption or frictional wear of the driving wire 116 caused by the rubbing motion between the driving wire 116 and the guide member 230.

(Third Embodiment)

Figure 10A:
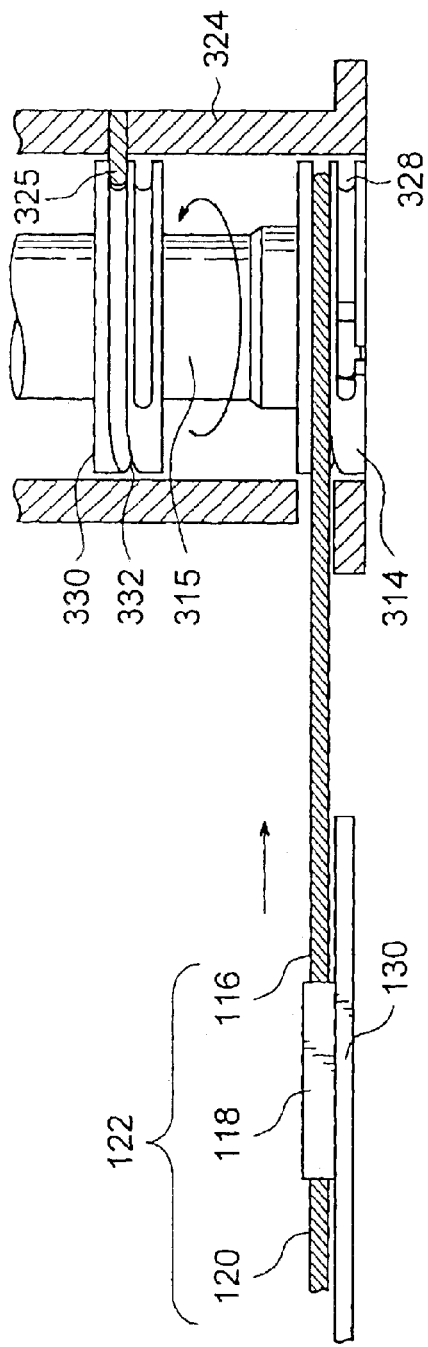
FIGS. 10A and 10B are diagrams schematically showing the constitution and the operation of the bending control mechanism of the endoscope according to the third embodiment of the invention.
Figure 10B:
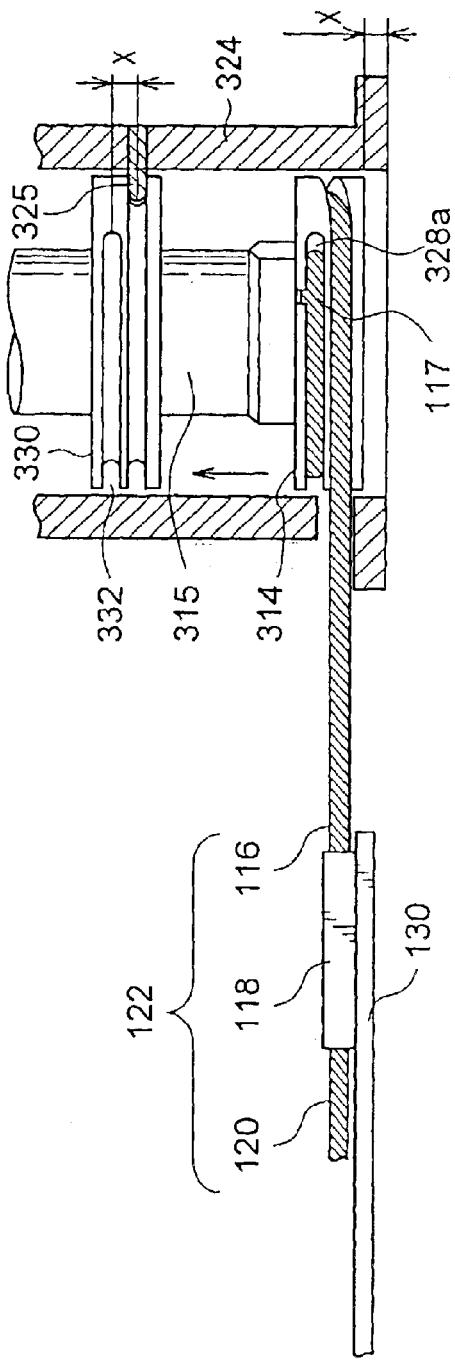

The following describes the bending control mechanism for the endoscope according to the third embodiment of the invention with reference to the accompanying drawings. FIGS. 10A and 10B are diagrams schematically showing the constitution and the operation of the bending control mechanism for the endoscope according to the third embodiment of the invention, in which FIG. 10A indicates the bending control mechanism when it stays in the neutral state, and FIG. 10B indicates the state of the bending control mechanism when the most driving wire 116 is wound round the pulley 314.

In the bending control mechanism according to the third embodiment as shown in FIGS. 10A and 10B, there is provided a pulley displacement mechanism, which enables a pulley 314 to move up and down in the axial direction thereof such that the extending direction of the driving wire 116 becomes substantially parallel to the guide face of the guide member 130 in correspondence with the height of the driving wire 116 wound round the pulley 314 in the axial direction thereof.

With provision of the pulley displacement mechanism like the above, it becomes possible to produce such a state that the driving wire 116 and the guide face of the guide member 130 mounting a connection member thereon become always substantially parallel to each other, the connection member being connected with the driving wire 116 with a bending wire 120. Because of this, there is no need for any excess force to be used for winding up the driving wire 116 round the pulley 314 by using the bending control lever 112 and the bending portion 108 can be controlled with smaller force. Furthermore, it becomes possible to prevent the consumption or frictional wear of the driving wire, which is caused by the rubbing motion between the driving wire116 and the wall face of the driving wire winding groove 328.

Here, there will be described in detail the concrete constitution of the pulley displacement mechanism according to the third embodiment, referring to the accompanying drawings. As shown in FIGS. 10A and 10B, the pulley displacement mechanism includes a cam of the cylinder type 330 which is provided on a pulley shaft portion 315 and a cam pin 325 which is provided on a support member 324 supporting the pulley 314 in the control portion such that the cam pin 325 fits to the cam groove 332 of the cylinder type cam 330. The cylinder type cam 330 may be arranged in a region, for instance the region between the pulley 314 and the bending control lever 112.

Similar to the pulley 10 as shown in FIGS. 5A and 5B, the pulley 314 according to this embodiment includes the driving wire winding groove 328 in the shape of a clockwise spiral, which is formed on the peripheral surface of the pulley 314 so as to extend in the peripheral direction of the pulley 314. The driving wire winding groove 328 is formed such that a plurality of stepped grooves are formed in the shape of a spiral along the axial direction of the shaft portion 315 from the end face side of the pulley 314 toward the side of the pulley shaft portion 315. Besides, as shown in FIG. 10B, the one end portion 328a of the driving wire winding groove 328 is fixedly connected with the end portion of one driving wire while the other end portion of the driving wire winding groove 328b is fixedly connected with the end portion of the other driving wire. In FIGS. 10A and 10B, the other driving wire is omitted.

As shown in FIGS. 10A and 10B, the above cylinder type cam 330 is constituted to have the same diameter as the pulley 314, and the cam groove 332 is formed in the shape of a spiral extending in the peripheral direction similar to the driving wire winging groove 328 of the pulley 314. Besides, the cam pin 325 fitting to the cam 332 is provided in the inner peripheral surface of the pulley support member 324 inserted in the shaft portion 315 of the pulley314.

According to the bending control mechanism of the third embodiment, if the pulley 314 is rotated by means of the bending control lever 112, the cylinder type cam 330 is turned linking with rotation of the pulley 314

If the cylinder type cam 330 is rotated, the cam pin 325 fixed through the pulley support member 324 is guided along the cam groove 332, thereby the cylinder cam 330 sliding in the axial direction, in link with which the pulley 314 also slides also in the axial direction. As a result, as shown in FIG. 10B, the pulley 314 is displaced in the axial direction by a distance of X.

As shown in FIG. 10B, in the state where the most driving wire 116 is wound round the pulley 314, the arrangement position of the cam pin 325 is determined such that the height in the axial direction of the driving wire 116 extending out from the driving wire winding groove 328 becomes the same as that of guide face (i.e. arrangement position of the connection member 118) of the guide member 130. Because of this, the extending direction of the driving wire 116 as extended out from the pulley 314 becomes always substantially parallel to the guide surface of the guide member 130.

In this case, when the most driving wire 116 is wound round the pulley 314 and the tension applied to the driving wire 116 is maximized, as the driving wire 116 and the guide face of the guide member 130 become substantially parallel to each other, the bending control lever 112 can be rotated without using any excess force.

Furthermore, according to the displacement mechanism of the third embodiment, the extending direction of the driving wire 116 can always be made to be substantially parallel to the guide face of the guide member 130, not limited to only when the tension applied to the driving wire 116 is maximized. Consequently, it becomes possible to more effectively prevent the consumption or frictional wear of the driving wire 116 which is caused by the rubbing motion between the driving wire 116 and the wall face of the driving wire winding groove 328, when winding the driving wire 116 round the pulley 314.

(Fourth Embodiment)

The following describes a bending control mechanism for the endoscope according to the fourth embodiment of the invention with reference to the accompanying drawings. FIGS. 11A and 11B are diagrams schematically showing the constitution and the operation of the bending control mechanism for the endoscope according to the fourth embodiment of the invention, in which FIG. 11A indicates the bending control mechanism when it is in the neutral state, and FIG. 11B indicates the bending control mechanism when the most driving wire 116 is wound round a pulley 414 at the time of executing the bending control.

The constitution of the pulley 414 according to the fourth embodiment is similar to that of the pulley 314 according to the third embodiment. A driving wire winding groove 428, an end portion 428a and an end portion 428b in the fourth embodiment correspond to the driving wire winding groove 328, the end portion 328a and the end portion 328b in the third embodiment as described in the above, respectively.

The pulley 414 of the fourth embodiment is also provided with a pulley displacement mechanism capable of displacing the pulley 414 in the axial direction thereof in the same way as the pulley 314 of the third embodiment. However, the former differs from the latter in that in the pulley displacement mechanism of the fourth embodiment, a cam pin 425 is provided on the pulley shaft portion 415 while a cam groove 426 is provided on the pulley support member 424.

To put it more concretely, as shown in FIGS. 11A and 11B, a cam groove 426 is provided along the inner face of the pulley support member 424 inserted in the shaft portion 415 of the pulley 414, the cam groove 426 being in the shape of a spiral extending in the peripheral direction of the above inner face of the pulley support member 424. Besides, the cam pin 425 fitting to the cam groove 426 is provided on the shaft portion 415 within a region between the pulley 414 and the bending control lever 112.

According to the bending control mechanism of the fourth embodiment, if the pulley 414 is rotated by the bending control lever 112, the cam pin 425 is turned linking with the rotation of the bending control lever 112. At this time, the cam pin 425 is guided along the cam groove 426 of the pulley support member 424, thereby the pulley 414 sliding in the axial direction. As a result, as shown in FIG. 11B, the pulley 414 is displaced in the axial direction by a distance of X.

As shown in FIG. 11B, the formation position of the cam groove 426 is determined such that, in the state where the most driving wire 116 is wound round the pulley 414, the height in the axial direction of the driving wire 116 extending out from the driving wire winding groove 428 becomes the same as that of the guide face (i.e. arrangement position of the connection member 118) of the guide member 130. As a result, the extending direction of the driving wire 116 as extended out from the pulley 414 becomes always substantially parallel to the guide surface of the guide member 130.

In this way, when the most driving wire 116 is wound round the pulley 414 and the tension applied to the driving wire 116 is maximized, as the driving wire 116 and the guide face of the guide member 130 become substantially parallel to each other, the bending control lever 112 can be rotated without using any excess force.

Furthermore, according to the displacement mechanism of the fourth embodiment, the extending direction of the driving wire 116 can be always substantially parallel to the guide face of the guide member 130, not limited to only when the tension applied to the driving wire 116 is maximized. As the result of this, it becomes possible to more effectively prevent the consumption or frictional wear of the driving wire 116 which is caused by the rubbing motion between the driving wire 116 and the wall face of the driving wire winding groove 428, when winding the driving wire round the pulley 414.

While several preferred embodiments of the invention have been shown and described with reference to the accompanying drawings, it is needless to say that the invention is not always limited to such embodiments. It will be apparent that one who is skilled in the art can make various changes and modifications without departing from the principle and spirit of the invention, the scope of which is defined in the appended claims, and it is understood that those changes and modifications naturally belong to the technical scope of the invention.

For instance, in the first embodiment, there is described an example wherein a driving wire winding groove in the shape of an anti-clockwise spiral is formed on the external peripheral surface of the pulley along the peripheral direction thereof. However, the invention is not always limited to this embodiment. If the driving wire is fixedly connected with the end portion of the driving wire winding groove on the end surface side of the pulley, the driving wire winding groove in the shape of clockwise spiral formed along the peripheral surface of the pulley can bring the same effect as the first embodiment.

Also, in the second, third and fourth embodiments, there are described examples wherein each driving wire winding groove in the shape of an anti-clockwise spiral is formed on the external peripheral surface of the pulley along the peripheral direction thereof. However, the invention is not always limited to these examples. If the driving wire is fixed to the end portion of the driving wire winding groove on the shaft side of the pulley, even the driving wire winding groove in the shape of anti-clockwise spiral formed on the peripheral surface of the pulley can bring the same effect.

As has been discussed so far, according to the bending control mechanism for the endoscope, when the tension applied to the driving wire is maximized, as the extending direction of the driving wire becomes substantially parallel to the guide face of the guide member, the control of the bending portion can be carried out by winding up the driving wire wound round the pulley with smaller force. Accordingly, there is provided an endoscope with the improved controllability.

Also, when the tension applied to the driving wire is maximized, as the extending direction of the driving wire becomes substantially parallel to the guide face of the guide member, it becomes possible to prevent the consumption or frictional wear of the driving wire which is caused by the rubbing motion between the driving wire wound round the pulley and the wall face of the driving wire winding groove provided along the peripheral surface of the pulley. Because of this, the durability of the driving wire can be improved.

Furthermore, as there is provided a pulley displacement mechanism capable of moving up and down the pulley in the axial direction thereof in correspondence with the height in the axial direction of the driving wire wound round the pulley such that the extending direction of the driving wire becomes substantially parallel to the guide face of the guide member, it becomes possible to make the extending direction of the driving wire be always substantially parallel to the guide face of the guide member. Because of this, it becomes possible to more effectively prevent the consumption or frictional wear of the driving wire which is caused by the rubbing between the driving wire and the wall face of the driving wire winding groove, when the driving wire is wound round the pulley.

What is claimed is:

1. A bending control mechanism for an endoscope comprising:

a bending portion provided in an insertion portion of the endoscope;

a bending wire extended out from said bending portion in order to control said bending portion;

a pulley made operable in linkage with a bending control lever through the shaft portion of the pulley, said bending control lever being provided in the control portion of said endoscope;

a driving wire winding groove as spirally formed on the outer peripheral surface of said pulley as well as in the peripheral direction of the pulley;

a driving wire wound around said driving wire winding groove of said pulley;

a connection member connecting said driving wire with said bending wire; and a guide member provided in said control portion and including said connection member slidably mounted thereon, wherein in the state where the most driving wire is wound round said pulley, a relative position between said pulley and said guide member is determined such that the extending direction of said driving wire is substantially in parallel with the guide surface of said guide member.

2. A bending control mechanism for an endoscope as claimed in claim 1, wherein in the state where the driving wire is wound maximally around said pulley, the direction of spiral turn of said driving wire winding groove is such a spiral turning direction that the direction in which said driving wire extends becomes substantially parallel to the guide surface of said guide member.

3. A bending control mechanism for an endoscope as claimed in claim 1, wherein in the state where the driving wire is wound maximally around said pulley, said guide member is arranged such that the extending direction of said driving wire is substantially in parallel with the guide surface of said guide member.

4. A bending control mechanism for an endoscope as claimed in claim 1, further comprising a pulley displacement mechanism which displaces said pulley in the axial direction of it such that the extending direction of said driving wire becomes substantially parallel to the guide surface of said guide member, in correspondence with the height of said driving wire wound round said pulley in the axial direction of said pulley.

5. A bending control mechanism for an endoscope as claimed in claim 4, wherein said pulley displacement mechanism is provided with a cam groove arranged on the shaft portion of said pulley, and a cam pin arranged on said pulley support member for supporting said pulley so as to fit said cam groove.

6. A bending control mechanism for an endoscope as claimed in claim 4, wherein said pulley displacement mechanism is provided with a cam arranged on said pulley support member for supporting said pulley, and a cam pin arranged on the shaft portion of said pulley so as to be fit said cam.

* * * * *